US00PP36596P2

(12) United States Plant Patent
Ranney et al.

(10) Patent No.: US PP36,596 P2
(45) Date of Patent: Apr. 15, 2025

(54) ***CORNUS* PLANT NAMED 'NCCH3'**

(50) Latin Name: ***Cornus* sp.**
Varietal Denomination: NCCH3

(71) Applicant: North Carolina State University, Raleigh, NC (US)

(72) Inventors: Thomas Ranney, Raleigh, NC (US); Nathan Lynch, Raleigh, NC (US); Andra Nus, Raleigh, NC (US); Irene Palmer, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 18/831,086

(22) Filed: Jun. 28, 2024

(51) Int. Cl.
*A01H 6/00* (2018.01)
*A01H 5/02* (2018.01)

(52) U.S. Cl.
USPC ..... Plt./220

(58) Field of Classification Search
USPC ..... Plt./220
CPC ..... A01H 6/00; A01H 5/02
See application file for complete search history.

(56) References Cited

PUBLICATIONS

Shearer, Kimberly et al. "Ploidy Levels and Relative Genome Sizes of Species, Hybrids, and Cultivars of Dogwood (*Cornus* spp.)," HortScience vol. 48, No. 7, pp. 825-830 (Jul. 2013).

*Primary Examiner* — Keith O. Robinson
(74) *Attorney, Agent, or Firm* — Meunier Carlin & Curfman LLC

(57) ABSTRACT

'NCCH3' is a new cultivar of flowering dogwood with a unique combination of traits including large white bracts, large glossy leaves, a fast growth rate, and showy fall color.

4 Drawing Sheets

Latin name: *Cornus* sp.
Varietal denomination: 'NCCH3'.

BACKGROUND OF THE INVENTION

The present invention relates to a new and distinct flowering dogwood tree cultivar hereinafter referred to by the cultivar name 'NCCH3'. This new dogwood was developed through a breeding program at a research nursery, located in Mills River, NC. 'NCCH3' was selected from a group of seedlings resulting from the open pollination of the female parent *Cornus* H2010-021-012, unpatented (*Cornus kousa* 'Greensleeves', unpatented x *Cornus florida* 'World's Fair', unpatented).

The first asexual propagation of 'NCCH3' was carried out in June 2018 by rooting stem cuttings in Mills River, North Carolina and has been asexually reproduced repeatedly by vegetative cuttings over a 7-year period. 'NCCH3' roots from softwood cuttings treated with a basal dip of 5,000-7,500 ppm indole butyric acid (potassium salt) in water. 'NCCH3' has been found to retain its distinctive characteristics through successive asexual propagations.

SUMMARY OF THE INVENTION

The following unique combination of characteristics of this new cultivar have been repeatedly observed when grown under standard horticultural practices in Mills River, North Carolina. These attributes in combination distinguish 'NCCH3' as unique cultivar of *Cornus*.

1. Large, white bracts.
2. Large, glossy foliage turning a brilliant combination of yellow, orange, and red colors in fall.

3. Vigorous growth, up to 3.0 meters tall in 4 years.
4. Triploid, with a 2C genome size of 5.22 pg.

'NCCH3' can be most closely compared to the cultivars of *Cornus kousa* 'Greensleeves' and *Cornus florida* 'World's Fair'. Both cultivars differ from 'NCCH3' in being diploids, having smaller leaves and inflorescence and having red to red purple fall color.

BRIEF DESCRIPTION OF THE DRAWINGS

This new dogwood is illustrated by the accompanying color photographs which show the form, foliage and inflorescences of the cultivar 'NCCH3'. The colors shown are as true as can be reasonably obtained by conventional photographic procedures. Colors in the photographs may differ slightly from the color values cited in the detailed botanical description, which accurately describe the colors of the new dogwood.

DETAILED BOTANICAL DESCRIPTION

Figure 1:
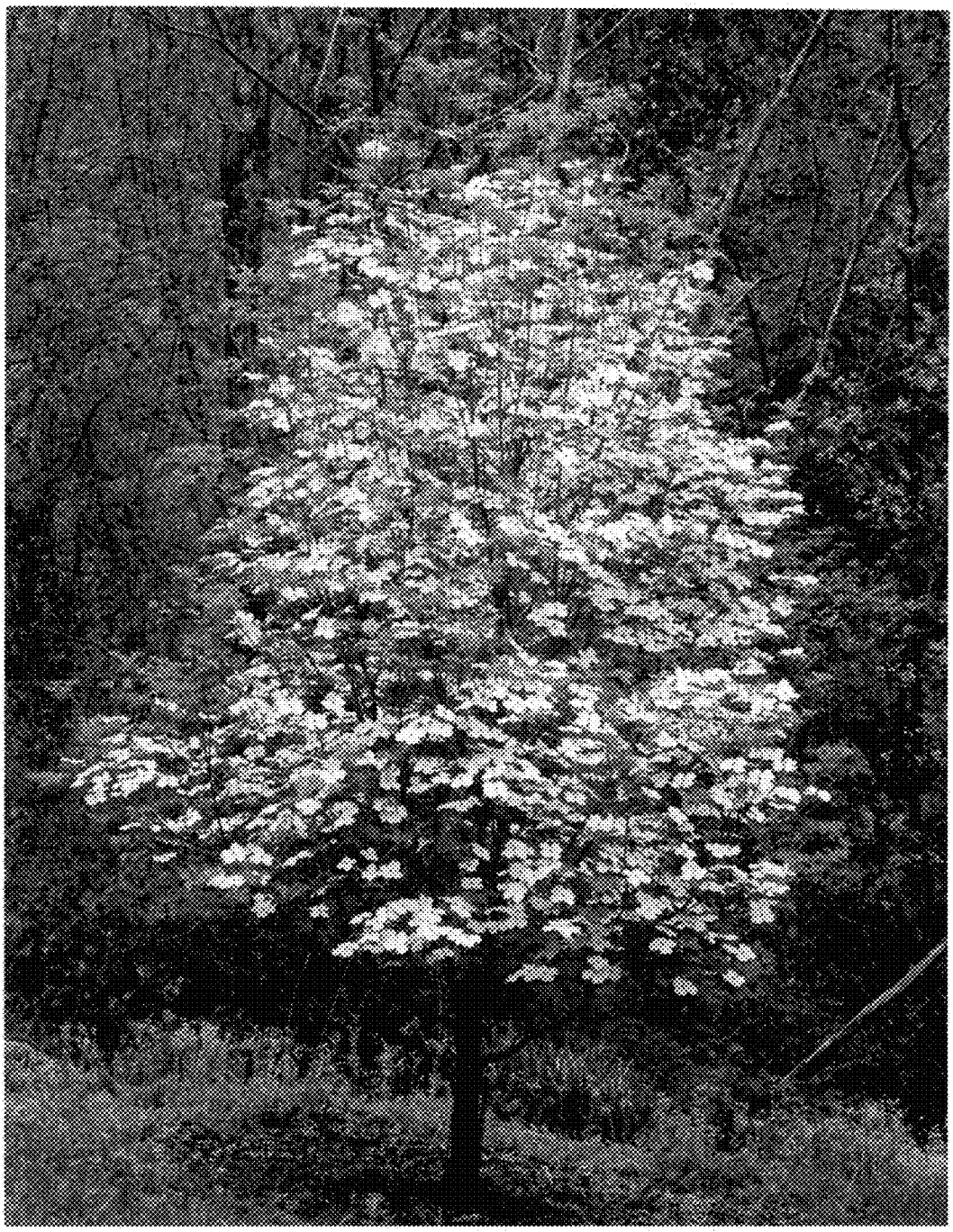
FIG. 1 is a color photograph showing a six-year-old, field-grown 'NCCH3'-tree in spring of 2023, in Arden, NC.
Figure 2:
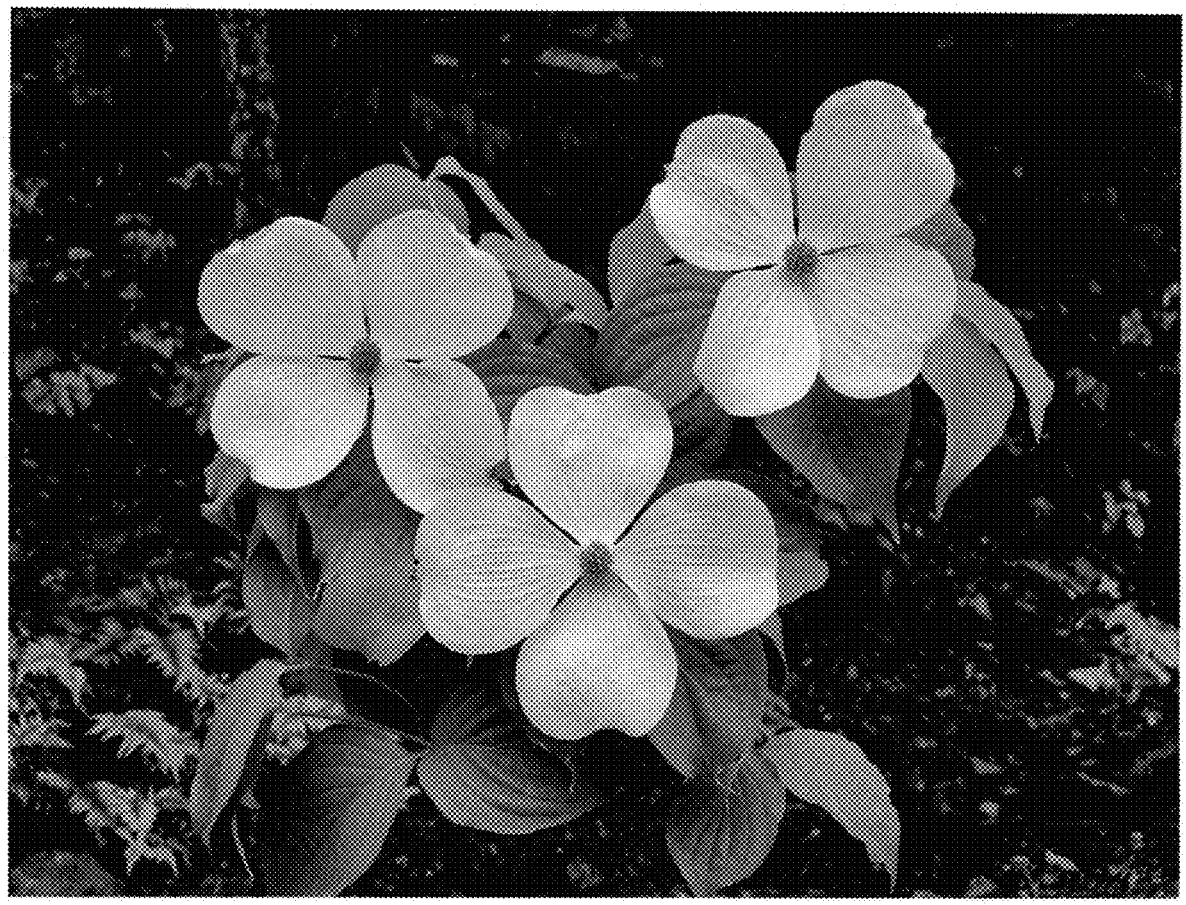
FIG. 2 is a color photograph showing the large inflorescences of a six-year-old, field-grown 'NCCH3'-tree in spring of 2023, in Arden, NC.
Figure 3:
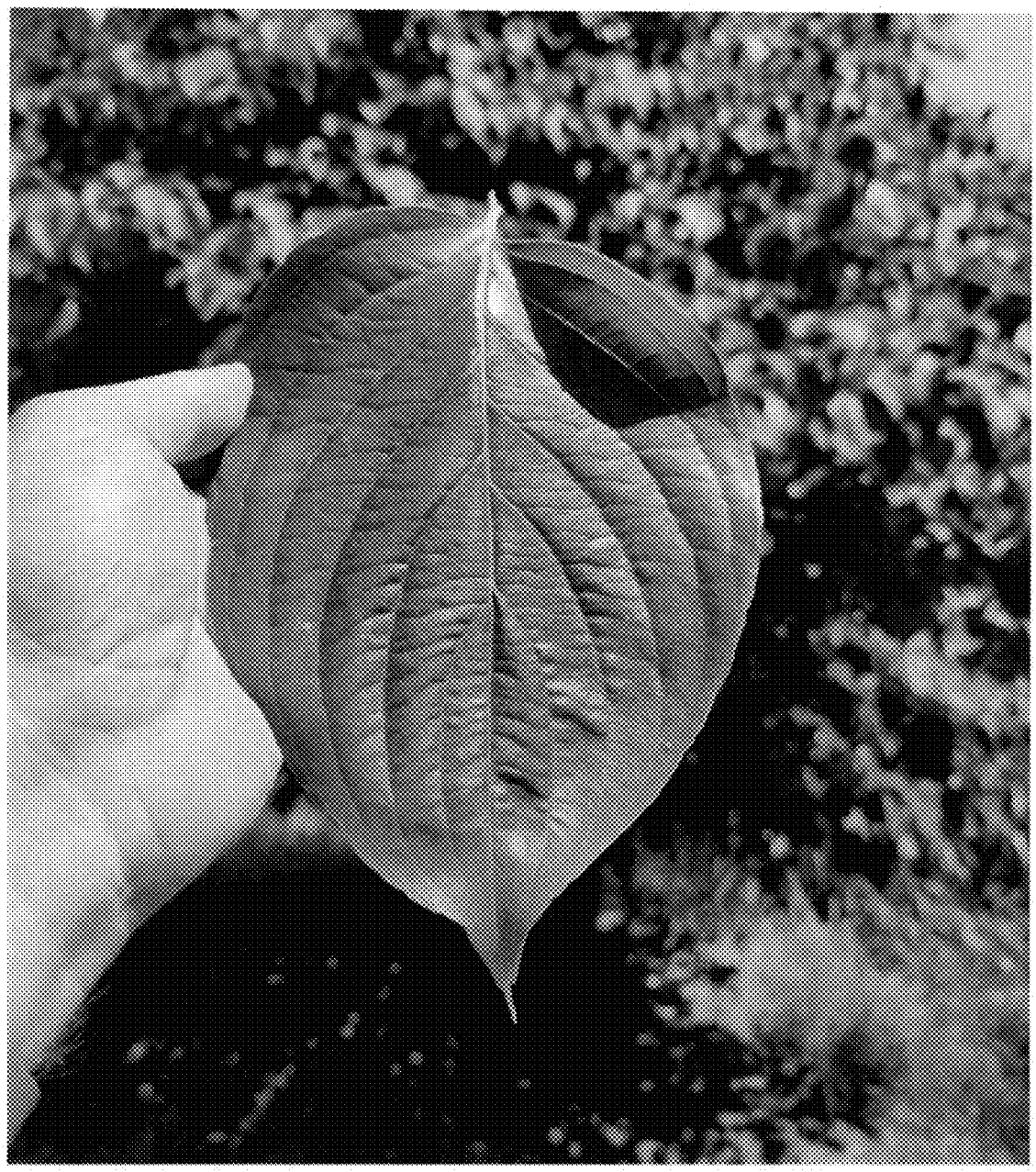
FIG. 3 is a color photograph of the large, clean, and glossy foliage of a six-year-old, field-grown 'NCCH3'-tree in August 2023, in Arden, NC.
Figure 4:
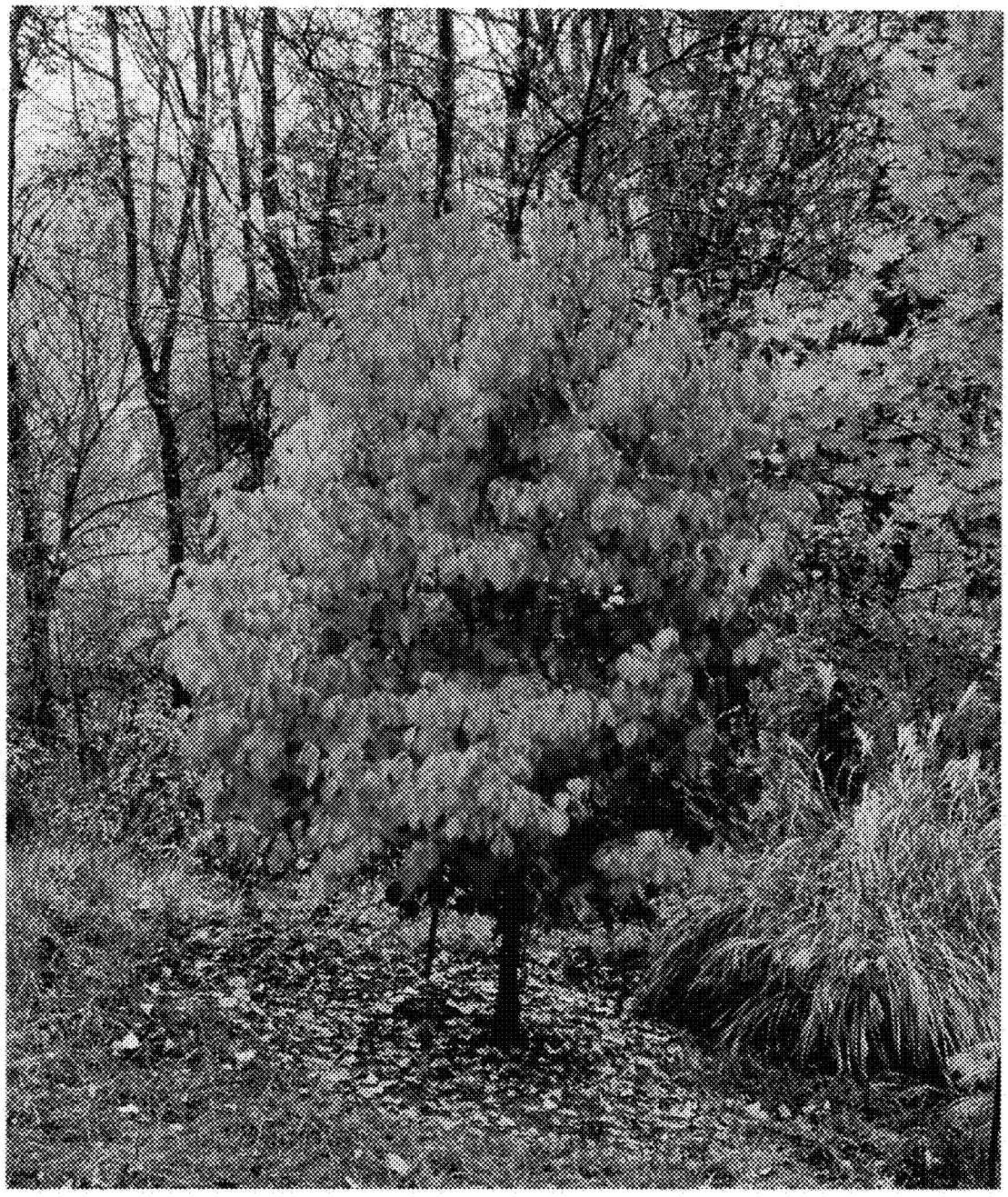
FIG. 4 is a color photograph of the fall color of a five-year-old field-grown 'NCCH3'-tree in the fall of 2022, in Arden, NC.

The following is a detailed description of the botanical characteristics of the new and distinct dogwood cultivar known by the denomination 'NCCH3'. The detailed description was taken on a four-year-old, field-grown plant in Mills River, North Carolina in 2022. All colors cited herein refer to The Royal Horticultural Society Colour Chart (The Royal Horticultural Society (R.H.S.), London, Sixth Edition). Where specific dimensions, sizes, colors, and other characteristics are given, it is to be understood that such characteristics are approximations or averages set forth as accurately as practicable.

Classification:

*Botanical name.*—*Cornus* 'NCCH3'.

*Common name.*—Flowering dogwood.

Parentage:

*Female parent.*—*Cornus* H2010-021-012 (*Cornus kousa* 'Greensleeves' x *Cornus florida* 'World's Fair', unpatented).

*Male parent.*—Unknown, open pollinated.

Plant description:

*Growth habit.*—Upright and rounded.

*Growth rate.*—Vigorous.

*Height.*—2.0 to 3.0 meters after 4 years.

*Width.*—1.2 to 2.0 meters after 4 years.

*Internode length.*—Avg. 8.7 cm (7 to 15 cm).

*Main stems per plant.*—1.

Shoots, branches, trunk:

*Shoots* (*current year's growth*).—Shoot length: Avg. 35.0 cm (Range 17 to 60 cm). Shoot diameter: About 0.3 cm. Color: Strong Yellow Green (RHS 144A). Texture: Finely pubescent.

*Shoots* (*prior year's growth*).—Stem length: Avg. 37.0 cm (21 to 60 cm). Stem diameter: About 0.4 cm. Color: Light Brownish Grey (RHS 201B). Texture: Finely pubescent.

*Branches* (*woody branches* 2-4 *years old*).—Branch length: About 180 cm. Branch diameter: Avg. 2.4 cm (1.5 to 4 cm). Color: Close to Light Brownish Grey (RHS 201B). Texture: Glabrous. Branch strength: Strong. Branching habit: Oppositely arranged. Upright and spreading. Number of lateral branches per stem: Many.

*Trunk* (*measured* 0.5 *meter from ground on a* 4-*year-old tree*).—Diameter: About 6 cm. Color: Light Olive Grey (RHS 197A). Texture: Glabrous.

Leaves:

*Type.*—Simple.

*Persistence.*—Deciduous.

*Arrangement.*—Opposite.

*Shape.*—Ovate.

*Venation.*—Pinnate.

*Vein number.*—5 to 7 vein pairs.

*Vein color, upper and lower.*—Yellowish Grey (RHS 194C).

*Length of lamina.*—Avg. 15 cm (10.2 to 20.0 cm).

*Width of lamina.*—Avg. 10 cm (6.5 to 15.5 cm).

*Color, emerging foliage.*—Upper: Strong Yellow Green (RHS 144A). Lower: Moderate Yellow Green (RHS 146C).

*Color, mature foliage.*—Upper: Moderate Olive Green (RHS 137B). Lower: Greyish Yellow Green (RHS 191A).

*Fall color.*—A vibrant blend of Vivid Orange Yellow (RHS 21A), Moderate Reddish Orange (RHS 35A), Strong Brown (RHS 172A) and Dark Red (RHS 183A).

*Texture, upper and lower surfaces.*—Pubescent.

*Apex.*—Acuminate.

*Base.*—Cuneate.

*Margins.*—Entire.

*Leaf attachment.*—Petiolate.

*Petiole.*—Length: Avg. 0.8 cm (0.5 to 1.0 cm). Diameter: About 0.2 cm. Color: Strong Yellow Green (RHS 145A). Texture: Pubescent.

*Number of leaves per lateral branch.*—Many.

*Number of leaves per shoot.*—4-8 pairs.

Inflorescence:

*Description.*—Rounded umbel of inconspicuous flowers subtended by showy bracts.

*Flowering season.*—Mid-April to May in Mills River, NC.

*Number of true flowers per inflorescence.*—About 32 (27 to 38).

*Fragrance.*—None.

*Inflorescence.*—Height: About 1 cm. Diameter: Avg. 14 cm (13 to 16 cm).

*Inflorescence bud.*—Shape: Globose. Height: About 0.6 cm. Diameter: About 1 cm. Color: Strong Yellow Green (RHS 145A) with a blush of Moderate Red (RHS 181A) on the tips of the bracts. Texture: Glabrous.

*Flower.*—True flower height: About 0.5 cm. True flower diameter: About 0.2 cm.

*Petals, true flowers.*—Arrangement: Cruciform. Number of petals per true flower: 4. Shape: Ovate. Length: About 0.3 cm. Width: About 0.1 cm. Color: Strong Yellow Green (RHS 145A) with tips of Light Yellow Green (RHS 145C). Texture: Glabrous.

*Bracts.*—Number: 4, rarely 5 or 6. Shape: Obovate. Length: Avg. 6.3 cm (5.5 to 7 cm). Width: Avg. 5.3 cm (4.8 to 5.5 cm). Color, upper and lower surface: Pale Yellow Green (RHS 157C). Texture: Glabrous. Apex: Acuminate. Base: Truncate. Margin: Entire.

*Pedicel.*—Length: Avg. 4.5 cm (4 to 5.5 cm). Diameter: About 0.3 cm. Color: Strong Yellow Green (RHS 145A). Texture: Pubescent. Strength: Strong.

*Reproductive organs, true flowers.*—Gynoecium: Pistil number: 1. Pistil length: About 0.3 cm. Stigma shape: Rounded. Stigma color: Light Yellow Green (RHS 145B). Style length: About 0.2 cm. Style color: Strong Yellow Green (RHS 145A). Androecium: Stamen number: 4.Anther shape: Rounded. Anther size: Less than 0.1 cm. Anther color: Dark Greenish Yellow (RHS 152D). Amount of pollen: None observed.

Fruit and seed:

*Fruit description.*—Cluster of drupes.

*Fruit shape.*—Globose

*Fruit diameter.*—Avg. 2.5 cm (2.3 to 2.8 cm).

*Fruit height.*—Avg. 2.0 cm (1.8 to 2.1 cm).

*Drupe number per cluster.*—About 38 (28 to 41).

*Drupe length.*—Avg. 1.0 cm (0.6 to 1.1 cm).

*Drupe width.*—Avg. 0.5 cm (0.4 to 0.6 cm).

*Drupe mature color.*—Vivid Red (RHS 45A).

*Drupe texture.*—Glabrous.

*Seed.*—None observed.

Ploidy: A triploid with a 2C genome size of 5.22 pg determined using DAPI fluorochrome and *Pisum sativum* 'Ctirad' (2C=8.76 pg) as an internal standard based on methods and reference values from Shearer and Ranney (2013).

Disease and insect resistance: No significant disease or insect pests have been observed including anthracnose (*Discula destructiva*) and powdery mildew (*Erysiphe pulchra*).

Cold hardiness: At least USDA zone 6b; testing has not been completed in colder zones.

COMPARISON WITH COMMERCIAL CULTIVARS

'NCCH3' is distinguished from *Cornus* H2010-021-012 (female parent), *Cornus florida* 'Appalachian Spring', unpatented, and *Cornus kousa* 'Greensleeves' in that 'NCCH3' is a triploid with larger leaves and inflorescences (Table 1). Additionally, 'NCCH3' has a combination of yellow, orange and red fall color.

TABLE 1

Comparison of cultivar 'NCCH3' with *Cornus florida* cultivar 'Appalachian Spring', *Cornus kousa*, cultivar 'Greensleeves' and *Cornus* H2010-021-012

| | Ploidy | Inflorescence diameter | Bracts | Leaves | Fall color |
|---|---|---|---|---|---|
| *Cornus* 'NCCH3' | 3x | Avg. 14 cm. | Obovate, acuminate apex. | Ovate, long acuminate. 10.2 to 20.0 cm long and 6.5 to 15.5 cm wide. | A combination of yellow, orange and red. |
| *Cornus florida* 'Appalachian Spring' | 2x | About 7.5 to 10 cm. | Obovate, emarginate apex. | Ovate, abruptly acuminate. 7.5 to 15 cm long and 3.8 to 7.6 inches wide. | Red purple. |
| *Cornus kousa* 'Greensleeves' | 2x | About 7.5 to 12 cm. | Ovate, acuminate apex. | Elliptic-ovate, acuminate apex. 5-10 cm long and 2-4.5 cm wide. | Red to red purple. |
| *Cornus* H2010-021-012 | 2x | Avg. 10.5 cm. | Ovate, acute apex. | Elliptic-ovate, acuminate apex. 6-12 cm long and 3 to 6 cm wide. | Red purple. |

What is Claimed is:

1. A new and distinct cultivar of flowering dogwood tree named 'NCCH3' as illustrated and described herein.

* * * * *